(12) United States Patent
Ma et al.

(10) Patent No.: US 9,695,417 B2
(45) Date of Patent: Jul. 4, 2017

(54) METHOD FOR LARGE-SCALE SYNTHESIS OF LONG-CHAIN NUCLEIC ACID MOLECULE

(76) Inventors: Qianjun Ma, Beijing (CN); Shaolu Li, Beijing (CN)

( * ) Notice: Subject to any disclaimer, the term of this patent is extended or adjusted under 35 U.S.C. 154(b) by 578 days.

(21) Appl. No.: 14/232,542

(22) PCT Filed: Jun. 13, 2012

(86) PCT No.: PCT/CN2012/000818
§ 371 (c)(1),
(2), (4) Date: Mar. 26, 2014

(87) PCT Pub. No.: WO2013/007099
PCT Pub. Date: Jan. 17, 2013

(65) Prior Publication Data
US 2014/0221255 A1 Aug. 7, 2014

(30) Foreign Application Priority Data
Jul. 12, 2011 (CN) .......................... 2011 1 0193635

(51) Int. Cl.
*C12N 15/10* (2006.01)
*C12P 19/34* (2006.01)

(52) U.S. Cl.
CPC ......... *C12N 15/1093* (2013.01); *C12N 15/10* (2013.01); *C12N 15/1031* (2013.01); *C12P 19/34* (2013.01)

(58) Field of Classification Search
None
See application file for complete search history.

(56) References Cited

U.S. PATENT DOCUMENTS 6,479,262 B1 11/2002 Delagrave

FOREIGN PATENT DOCUMENTS

| CA | 2616762 | 8/2007 |
|---|---|---|
| CN | 101133166 B | 2/2011 |
| WO | WO-2007/040592 A1 | 4/2007 |
| WO | WO-2007/086935 A2 | 8/2007 |
| WO | WO2007/086935 A2 | 8/2007 |
| WO | WO-2007/091064 A1 | 8/2007 |

OTHER PUBLICATIONS

Jang, J. H. and H. B. Lim. Characterization and analytical application of surface modified magnetic nanoparticles. Microchemical Journal 94, No. 2 (2010): 148-158.*
Kuzmin A, Poloukhtine A, Wolfert MA, Popik VV. Surface functionalization using catalyst-free azide-alkyne cycloaddition. Bioconjug Chem. Nov. 17, 2010; 21(11):2076-85. Epub Oct. 21, 2010.*
Tian J, Gong H, Sheng N, Zhou X, Gulari E, Gao X, Church G. Accurate multiplex gene synthesis from programmable DNA microchips. Nature. Dec. 23, 2004; 432(7020):1050-4.*
Zhou X, Cai S, Hong A, You Q, Yu P, Sheng N, Srivannavit O, Muranjan S, Rouillard JM, Xia Y, Zhang X, Xiang Q, Ganesh R, Zhu Q, Matejko A, Gulari E, Gao X. Microfluidic PicoArray synthesis of oligodeoxynucleotides and simultaneous assembling of multiple DNA sequences. Nucleic Acids Res. Oct. 11, 2004; 32(18):5409-17. Print 2004.*
Marble HA, Davis RH. RNA transcription from immobilized DNA templates. Biotechnol Prog. Jul.-Aug. 1995; 11(4):393-6.*
Milligan JF, Groebe DR, Witherell GW, Uhlenbeck OC. Oligoribonucleotide synthesis using T7 RNA polymerase and synthetic DNA templates. Nucleic Acids Res. Nov. 11, 1987; 15(21):8783-98.*
Chinese Examination Report 100085, dated Nov. 2, 2014.
Chinese Examination Report 100085, dated Jul. 7, 2015.
Supplementary European Search Report (Jan. 15, 2015).
Jingdong, Tian et al., "Advancing High-Input Gene Synthesis Technology+", Molecular Biosystems, Royal Society of Chemistry, GB, vol. 5, No. 7 (Jul. 1, 2009), pp. 714-722.
Jingdong, Tian et al., "Parallel on-chip Gene Synthesis and Application to Optimization of Protein Expression", Nature Biotechnology, vol. 29, No. 5, (Apr. 24, 2011), pp. 449-452.
Matzas, M. et al., High-fidelity gene synthesis by retrieval of . . . Nature Biotechnology, vol. 28, No. 12, (Dec. 31, 2010), pp. 1291-1294, and Online Methods, ISSN: 1087-0156.
Algire, M., Megabases for kilodollars, Nature Biotechnology, vol. 28, No. 12, (Dec. 31, 2010), pp. 1272-1273, ISSN: 1087-0156.
International Search Report issued in PCT/CN2012/000818.
International Preliminary Report (Jun. 13, 2012).
Written Opinion (Jun. 13, 2012).
European Examination Report, Application No. 12 810 692.9-1404, dated Apr. 21, 2016.
Randall A. Hughes et al., Gene Synthesis: Methods and Applications; Methods in Enzymology vol. 498.
Jingdon Tian et al., Advancing High-Throughput Gene Synthesis Technology.
Japan Examination Report, Application No. 2014-519377; dated Apr. 26, 2016.

\* cited by examiner

*Primary Examiner* — Samuel Woolwine
*Assistant Examiner* — Olayinka Oyeyemi
(74) *Attorney, Agent, or Firm* — Goodwin

(57) ABSTRACT

Systems and methods for synthesizing long-chain nucleic acids molecules are disclosed. The systems and methods described in this application use a Ligation-Purification-Amplification ("LPA") technique. The LPA technique requires first producing nucleotide sequences with the length of at least 500 bp-1 kbp by assembling smaller oligonucleotide fragments (30 bp-200 bp). The assembled nucleotide sequences are then purified and amplified. This technology can be used to achieve parallel amplification of three or more nucleotide sequences at the same time. In embodiments of the invention, a solid-phase ligation-purification method is adopted, in which nucleic acid molecules are fixed on the surface of beads or other solid particles in order to rapidly purify products obtained from the ligation reaction.

11 Claims, 8 Drawing Sheets

SEQUENCE LISTING

<160> NUMBER OF SEQ ID NOS: 102

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tcgagcggcc gcccgggcag gt                                               22

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agcgtggtcg cggccgaggt                                                  20

<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tcacaggatg gctaatacga aggacactgt agaaagcgtg gtcgc                      45

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tcgagcggcc gcccgggcag gtgggacagc agaggaa                               37

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
acctcggccg cgaccacgct ttctacagtg tcct                                  34

<210> SEQ ID NO 6
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tggaggaatg tgctgtcact tgttcaaata gtcacaaccc ttctaactcc aaccagcct       59

<210> SEQ ID NO 7
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cacaggagca ccaaaatcac atttaaggaa cacgaagtcg actctgctct ggttgtaga       59

<210> SEQ ID NO 8
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gagtgaacac cctcatgatg aagaggagga agctctaaac attcccccag aaaatcaaa       59

<210> SEQ ID NO 9
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
atgaccatga ggaggaggag gggaaagcgc cagtgccccc cagacaccat gacaagtcc       59

<210> SEQ ID NO 10
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
aactcttacc ggcatcgtga agtctctttc ttggcattgg atgaacagaa agtttgctc       59

<210> SEQ ID NO 11
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cgctcaggat gttgccaggg attactccaa tcccaaatgg gatgaaacct cacttggct       59

<210> SEQ ID NO 12
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tccgcgtcac tggagatgaa ggaggcagct gccaccgaga tccgccgagt catcacagg       59

<210> SEQ ID NO 13
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tcgcgtccca gaaagcttaa gaaactgtgt gaacaaggag ttatttgtca catcagcgc    59

<210> SEQ ID NO 14
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tgactatttg aacaagtgac agcacattcc tccattcctc tgctgtccca cctgcccgg    59

<210> SEQ ID NO 15
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cgtgttcctt aaatgtgatt ttggtgctcc tgtgaggctg gttggagtta aagggttg    59

<210> SEQ ID NO 16
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
agcttcctcc tcttcatcat gagggtgttc actctctaca accagagcag agtcgactt    59

<210> SEQ ID NO 17
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
actggcgctt tccccctcctc ctcctcatgg tcattttgat tttctggggg aatgtttag    59

<210> SEQ ID NO 18
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ccaagaaaga gacttcacga tgccggtaag agttggactt gtcatggtgt ctgggggc    59

```
<210> SEQ ID NO 19
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gggattggag taatccctgg caacatcctg agcggagcaa actttctgtt catccaatg      59

<210> SEQ ID NO 20
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tggcagctgc ctccttcatc tccagtgacg cggaagccaa gtgaggtttc atcccattt      59

<210> SEQ ID NO 21
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gttcacacag tttcttaagc tttctgggac gcgacctgtg atgactcggc ggatctcgg      59

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggccgaggtg cgctgatgtg acaaataact cctt                                 34

<210> SEQ ID NO 23
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cattctccac ttcttgttcc ccactgacag cctcccaccc ccatctctcc ctcccctgc      59

<210> SEQ ID NO 24
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cattttgggt tttgggtctt tgaacccttg cttgcaatag gtgtgcgtca gaagcaccc      59

<210> SEQ ID NO 25
```

<210> SEQ ID NO 25
<211> LENGTH: 59
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 25
aggacttcca tttgctttgt cccggggctc cactgaacaa gttggcctgc actggtgtt        59

<210> SEQ ID NO 26
<211> LENGTH: 59
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 26
ttgttgtggg gaggaggatg gggagtagga cataccagct tagattttaa ggtttttac        59

<210> SEQ ID NO 27
<211> LENGTH: 59
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 27
tgtgagggat gtttgggaga tgtaagaaat gttcttgcag ttaagggtta gtttacaat        59

<210> SEQ ID NO 28
<211> LENGTH: 59
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 28
cagccacatt ctaggtaggg gcccacttca ccgtactaac cagggaagct gtccctcac        59

<210> SEQ ID NO 29
<211> LENGTH: 59
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 29
tgttgaattt tctctaactt caaggcccat atctgtgaaa tgctggcatt tgcacctac        59

<210> SEQ ID NO 30
<211> LENGTH: 59
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 30
ctcacagagt gcattgtgag ggttaatgaa ataatgtaca tctggccttg aaaccacct        59

<210> SEQ ID NO 31
<211> LENGTH: 59

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tttattacat ggggtctaga acttgacccc cttgagggtg cttgttccct ctccctgtt       59

<210> SEQ ID NO 32
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ggtcggtggg ttggtagttt ctacagttgg gcagctggtt aggtagaggg agttgtcaa       59

<210> SEQ ID NO 33
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gtctctgctg gcccagccaa accctgtctg acaacctctt ggtgaacctt agtacctaa       59

<210> SEQ ID NO 34
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gaggctgtca gtggggaaca agaagtggag aatgttcctc tgctgtccca cctgcccgg       59

<210> SEQ ID NO 35
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
caagcaaggg ttcaaagacc caaaacccaa aatggcaggg gagggagaga tgggggtgg       59

<210> SEQ ID NO 36
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
agtggagccc cgggacaaag caaatggaag tcctgggtgc ttctgacgca cacctattg       59

<210> SEQ ID NO 37
<211> LENGTH: 59
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 37
tatgtcctac tccccatcct cctccccaca acaaaacacc agtgcaggcc aacttgttc      59

<210> SEQ ID NO 38
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gaacatttct tacatctccc aaacatccct cacagtaaaa accttaaaat ctaagctgg      59

<210> SEQ ID NO 39
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
acggtgaagt gggcccctac ctagaatgtg gctgattgta aactaaccct taactgcaa      59

<210> SEQ ID NO 40
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
agatatgggc cttgaagtta gagaaaattc aacagtgagg gacagcttcc ctggttagt      59

<210> SEQ ID NO 41
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ttatttcatt aaccctcaca atgcactctg tgaggtaggt gcaaatgcca gcatttcac      59

<210> SEQ ID NO 42
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42 caaggggtc aagttctaga ccccatgtaa taaaaggtgg tttcaaggcc agatgtaca      59

<210> SEQ ID NO 43
<211> LENGTH: 59
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 43
ttgtcagaca gggtttggct gggccagcag agacttgaca actccctcta cctaaccag      59

<210> SEQ ID NO 44
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ctgcccaact gtagaaacta ccaacccacc gaccaacagg gagagggaac aagcaccct      59

<210> SEQ ID NO 45
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ggccgaggtt taggtactaa ggttcaccaa gagg                                 34

<210> SEQ ID NO 46
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
cggtgagcag gatgattttt atgaagtgag cctggacaac aacgtggagc ctgcaccag      59

<210> SEQ ID NO 47
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gagcggccag ggagggttct ccccatgaca acccccggt acagcagatc gtgcagctg       59

<210> SEQ ID NO 48
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tctcctgtca tgcaggacac ctaggagcac ccaggcttgc ccagcaaacc ctgcgtgcc      59

<210> SEQ ID NO 49
<211> LENGTH: 59
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 49
attcttctac caggcagccg agaacaggga gataaacatc atcatcttct aagagctgg      59

<210> SEQ ID NO 50
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
tcaagaaatt taaacaaca acaacaaaaa gttacggggt tcatctccta cacaattca      59

<210> SEQ ID NO 51
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
tttactccat ttgaatgcta gagccactca catttatttg tgtttctaat ttaccgttt      59

<210> SEQ ID NO 52
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
aaacatgacc ccagagtctg cactggagga gctgctggcc gttcaggtgg agctggagc      59

<210> SEQ ID NO 53
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
cggttaatgc ccaagccagg aaggcctttt ctcggcagcg ggaaaagatg gagcggagg      59

<210> SEQ ID NO 54
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
cgcaagcccc acctagaccg cagaggcgcc gtcatccaga gcgtccctgg cttctgggc      59

<210> SEQ ID NO 55
<211> LENGTH: 59
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 55
caatgttatt gcaaaccacc cccagatgtc agccctgatc actgacgaag atgaagaca        59

<210> SEQ ID NO 56
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
tgctgagcta catggtcagc ctggaggtgg aagaagagaa gcatcctgtt catctctgc        59

<210> SEQ ID NO 57
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
aagatcatgt tgttctttcg gagtaacccc tacttccaga ataaagtgat taccaaggg        59

<210> SEQ ID NO 58
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ccctatgagt gcaatgaatg tgggaaatcc ttcataagga gctcgagcct cattcgcca        59

<210> SEQ ID NO 59
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ttatcagatc cacacagaag tgaaacagta tgaatgcaaa gaatgtggga aggcattcc        59

<210> SEQ ID NO 60
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gtcatcgctc agaccttatt gaacaccaga gaattcacac cggagagaga ccctttgaa        59

<210> SEQ ID NO 61
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
tgcaatgagt gtgggaaagc ctttattcgg agttcaaagc tcattcagca tcagaggat    59

<210> SEQ ID NO 62
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
caggctcact tcataaaaat catcctgctc accgttcctc tgctgtccca cctgcccgg    59

<210> SEQ ID NO 63
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gggttgtcat ggggagaacc ctccctggcc gctcctggtg caggctccac gttgttgtc    59

<210> SEQ ID NO 64
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
ctgggtgctc ctaggtgtcc tgcatgacag gagacagctg cacgatctgc tgtaccggg    59

<210> SEQ ID NO 65
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
tatctccctg ttctcggctg cctggtagaa gaatggcacg cagggtttgc tgggcaagc    59

<210> SEQ ID NO 66
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
taactttttg ttgttgttgt tttaaatttc ttgaccagct cttagaagat gatgatgtt    59

<210> SEQ ID NO 67
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
aatgtgagtg gctctagcat tcaaatggag taaatgaatt gtgtaggaga tgaaccccg    59

<210> SEQ ID NO 68
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
cagctcctcc agtgcagact ctggggtcat gtttaaacgg taaattagaa acacaaata    59

<210> SEQ ID NO 69
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
cgagaaaagg ccttcctggc ttgggcatta accggctcca gctccacctg aacggccag    59

<210> SEQ ID NO 70
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
tgacggcgcc tctgcggtct aggtggggct tgcgcctccg ctccatcttt tcccgctgc    59

<210> SEQ ID NO 71
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
ggctgacatc tgggggtggt ttgcaataac attggcccag aagccaggga cgctctgga    59

<210> SEQ ID NO 72
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
tcttccacct ccaggctgac catgtagctc agcatgtctt catcttcgtc agtgatcag    59

<210> SEQ ID NO 73
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73 agtagggggtt actccgaaag aacaacatga tcttgcagag atgaacagga tgcttctct    59

<210> SEQ ID NO 74
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
tgaaggattt cccacattca ttgcactcat agggcccttg gtaatcactt tattctgga    59

<210> SEQ ID NO 75
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ttcatactgt ttcacttctg tgtggatctg ataatggcga atgaggctcg agctcctta    59

<210> SEQ ID NO 76
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
aactccgaat aaaggctttc ccacactcat tgcattcaaa gggtctctct ccggtgtga    59

<210> SEQ ID NO 77
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
attctctggt gttcaataag gtctgagcga tgacggaatg ccttcccaca ttctttgca    59

<210> SEQ ID NO 78
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ggccgaggta tcctctgatg ctgaatgagc tttg    34

<210> SEQ ID NO 79
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)

<223> OTHER INFORMATION: a, c, t, g, unknown or other

<400> SEQUENCE: 79
nnnnngaatg ctgtcacttg ttcaaatagt cacaaccctt ctaactccaa ccagcct    57

<210> SEQ ID NO 80
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, c, t, g, unknown or other

<400> SEQUENCE: 80
tggagnnnnn tgctgtcact tgttcaaata gtcacaaccc ttctaactcc aaccagcct    59

<210> SEQ ID NO 81
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(15)
<223> OTHER INFORMATION: a, c, t, g, unknown or other

<400> SEQUENCE: 81
tggaggaatg nnnnntcact tgttcaaata gtcacaaccc ttctaactcc aaccagcct    59

<210> SEQ ID NO 82
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, c, t, g, unknown or other

<400> SEQUENCE: 82
nnnnnttacc ggcatcgtga agtctctttc ttggcattgg atgaacagaa agtttgctc    59

<210> SEQ ID NO 83
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(9)
<223> OTHER INFORMATION: a, c, t, g, unknown or other

<400> SEQUENCE: 83
actcnnnnng gcatcgtgaa gtctctttct tggcattgga tgaacagaaa gtttgctc    58

<210> SEQ ID NO 84
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(17)
<223> OTHER INFORMATION: a, c, t, g, unknown or other

<400> SEQUENCE: 84
aactcttacc ggnnnnntga agtctctttc ttggcattgg atgaacagaa agtttgctc       59

<210> SEQ ID NO 85
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other

<400> SEQUENCE: 85
nnnnaggatg ttgccaggga ttactccaat cccaaatggg atgaaacctc acttggct       58

<210> SEQ ID NO 86
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, c, t, g, unknown or other

<400> SEQUENCE: 86
cgctcnnnnn gttgccaggg attactccaa tcccaaatgg gatgaaacct cacttggct       59

<210> SEQ ID NO 87
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(15)
<223> OTHER INFORMATION: a, c, t, g, unknown or other

<400> SEQUENCE: 87
cgctcaggat nnnnncaggg attactccaa tcccaaatgg gatgaaacct cacttggct       59

<210> SEQ ID NO 88
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, c, t, g, unknown or other

<400> SEQUENCE: 88
nnnnngtcac tggagatgaa ggaggcagct gccaccgaga tccgccgagt catcacagg       59

<210> SEQ ID NO 89
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(8)
<223> OTHER INFORMATION: a, c, t, g, unknown or other

<400> SEQUENCE: 89
tccgcnnntg agatgaagg aggcagctgc caccgagatc cgccgagtca tcacagg         57

<210> SEQ ID NO 90
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(15)
<223> OTHER INFORMATION: a, c, t, g, unknown or other

<400> SEQUENCE: 90
tccgcgtcac nnnnnatgaa ggaggcagct gccaccgaga tccgccgagt gccaccgaga     60
tccgccgagt catcacagg                                                  79

<210> SEQ ID NO 91
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, c, t, g, unknown or other

<400> SEQUENCE: 91
nnnnngtggg gaggaggatg gggagtagga cataccagct tagattttaa ggtttttac      59

<210> SEQ ID NO 92
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, c, t, g, unknown or other

<400> SEQUENCE: 92
ttgttnnnnn gaggaggatg gggagtagga cataccagct tagattttaa ggtttttac      59

<210> SEQ ID NO 93
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: modified_base
<222> LOCATION: (11)..(15)
<223> OTHER INFORMATION: a, c, t, g, unknown or other

<400> SEQUENCE: 93
ttgttgtggg nnnnnggatg gggagtagga cataccagct tagattttaa ggttttttac      59

<210> SEQ ID NO 94
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, c, t, g, unknown or other

<400> SEQUENCE: 94
nnnnngggat gtttgggaga tgtaagaaat gttcttgcag ttaagggtta gtttacaat       59

<210> SEQ ID NO 95
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, c, t, g, unknown or other

<400> SEQUENCE: 95
tgtgannnnn gtttgggaga tgtaagaaat gttcttgcag ttaagggtta gtttacaat       59

<210> SEQ ID NO 96
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(15)
<223> OTHER INFORMATION: a, c, t, g, unknown or other

<400> SEQUENCE: 96
tgtgagggat nnnnnggaga tgtaagaaat gttcttgcag ttaagggtta gtttacaat       59

<210> SEQ ID NO 97
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, c, t, g, unknown or other

<400> SEQUENCE: 97
nnnnntgacc ccagagtctg cactggagga gctgctggcc gttcaggtgg agctggagc       59

<210> SEQ ID NO 98
```

```
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, c, t, g, unknown or other

<400> SEQUENCE: 98
aaacannnnn ccagagtctg cactggagga gctgctggcc gttcaggtgg agctggagc    59

<210> SEQ ID NO 99
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(15)
<223> OTHER INFORMATION: a, c, t, g, unknown or other

<400> SEQUENCE: 99
aaacatgacc nnnnngtctg cactggagga gctgctggcc gttcaggtgg agctggagc    59

<210> SEQ ID NO 100
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, c, t, g, unknown or other

<400> SEQUENCE: 100
nnnnntgagt gtgggaaagc cttattcgga gttcaaagct cattcagcat cagaggat     58

<210> SEQ ID NO 101
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, c, t, g, unknown or other

<400> SEQUENCE: 101
tgcaannnnn gtgggaaagc ctttattcgg agttcaaagc tcattcagca tcagaggat    59

<210> SEQ ID NO 102
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(15)
<223> OTHER INFORMATION: a, c, t, g, unknown or other
```

```
<400> SEQUENCE: 102
tgcaatgagt nnnnnaaagc ctttattcgg agttcaaagc tcattcagca tcagaggat      59
```

METHOD FOR LARGE-SCALE SYNTHESIS OF LONG-CHAIN NUCLEIC ACID MOLECULE

CONTINUITY DATA

The present application claims priority to Chinese Patent Application No. 201110193635.4, filed Jul. 12, 2011, along with PCT/CN2012/000818, filed Jun. 13, 2013, the entire disclosures of which are incorporated herein by reference.

SEQUENCE LISTING

The present application contains a Sequence Listing, shown in table form in the Detailed Description, which has been submitted electronically in ASCII format and is hereby incorporated by reference in its entirety. Said ASCII copy, created on Jan. 24, 2014, is named BVS001US_SL.txt and is 26,426 bytes in size.

TECHNICAL FIELD

The present invention relates to systems and methods for the large-scale, low cost synthesis of long-chain nucleic acid molecules by assembling short-chain oligonucleotides.

BACKGROUND OF THE INVENTION

In recent years, developments in the field of synthetic biology have allowed researchers to synthesize a number of intermediates with potential applications in, for instance, the bio-energy or pharmaceuticals fields, by changing bacterial or cellular metabolic processes. For example, in 2006, scientists used engineered yeast to synthesize artemisinin intermediates, increasing the yield to reach 115 mg/mL (Ro, D. K. et al. *Nature,* 2006, 440: 940-943). In 2009, George Church's group accelerated the evolution of *E. coli* to increase the yield of lycopene by fivefold, through introducing a set of oligonucleotides to modify the bacteria's genome (Wang, H. et al. *Nature,* 2009, 460: 894-898).

Scientists have also begun synthesizing complete genomes for living organisms. In 2008, the genome of *Mycoplasma Genitalium,* measuring 582 kb in length, was successfully synthesized. In 2010, scientists assembled a modified genome of about one million base pairs, and used it to produce a self-replicating *Mycoplasma Mycoides* (Gibson, D, et al. *Science,* 2010, 329:52-56.

One key development which has prompted significant growth in the field of synthetic biology is the maturation of gene synthesis technology. In recent years, DNA microarray technology has given researchers the ability to synthesize genes on a large scale. Indeed, at present, one microarray can synthesize millions of oligonucleotides. However, the lengths of these oligonucleotides range generally between 60 bp to 200 bp. Assembling these oligonucleotides into genes with sufficient length (i.e., greater than 1 kb) is a current challenge to researchers, particularly in circumstances where thousands of long-chain genes are needed.

Currently, there exist two related strategies for addressing these problems. The first is to continue to improve synthesis techniques and develop new approaches to increasing the length of each oligonucleotide. The second is to develop an effective method to assemble millions of short oligonucleotides into long-chain genes in parallel. However, the first strategy depends on, and is still awaiting, further breakthroughs in new technologies. And while there has been some development with regards to the second strategy, these established approaches still have certain drawbacks. For instance, Church successfully synthesized 47 genes (measuring 35 kb) by selectively amplifying and assembling a group of microchip-synthesized oligonucleotides (Kosuri, S. et al. *Nature Biotechnology,* 2010, 28(12):1295-1299). Church accomplished this by assembling a group of amplified oligonucleotides into a long-chain nucleotide sequence using a DNA microchip. Jingdong Tian's group also achieved synthesis of 74 genes (measuring 30 kb) by dividing a microarray into distinct physical units, and then performing parallel synthesis, amplification and assembly (Quan, J. et al. *Nature Biotechnology,* 2011, 29(5):448-452. However, both methods are not only very costly, but are also limited in synthetic throughput.

This present application describes simpler and more feasible systems and methods for synthetically assembling thousands of oligonucleotides into multiple nucleotide sequences in parallel.

SUMMARY OF THE INVENTION

In one aspect of the invention, a method for synthesizing long-chain nucleic acid molecules through assembling short-chain oligonucleotides is disclosed, the method comprising: phosphorylating a set of short-chain oligonucleotides; modifying at least one of the short-chain oligonucleotides in the set with a first chemical group; annealing the set of short-chain oligonucleotides; ligating the set of short-chain oligonucleotides in the presence of a ligase, wherein the ligation produces at least one double-stranded long-chain nucleotide sequence; immobilizing the at least one double-stranded long-chain nucleotide sequence on solid particles modified with a second chemical group, wherein the first chemical group and second chemical group have an affinity for one another; purifying the at least one double-stranded long-chain nucleotide sequence; and, after purification, amplifying the at least one double-stranded long-chain nucleotide sequence.

DETAILED DESCRIPTION OF PREFERRED EMBODIMENTS

The systems and methods described in this application aim to achieve large-scale synthesis of long-chain nucleic acid molecule, that is, first synthesizing short-chain oligonucleotides, and then assembling these short-chain oligonucleotides into long-chain nucleotide sequences.

In this application, the terms "nucleotide sequence," "oligonucleotide," "oligomer" and/or "nucleic acid molecule" are discussed with reference to ribonucleic acid ("RNA"), deoxyribonucleic acid ("DNA") and/or their derivatives (including hybrids).

The systems and methods described in this application use a Ligation-Purification-Amplification ("LPA") technique. The LPA technique requires first producing nucleotide sequences with the length of at least 500 bp-1 kbp by assembling smaller oligonucleotide fragments (30 bp-200 bp). The assembled nucleotide sequences are then purified and amplified. This technology can be used to achieve parallel amplification of three or more nucleotide sequences at the same time by use of polymerase chain reaction ("PCR"), if all the assembled nucleotide sequences are flanked with the same sequences. In embodiments of the invention, a solid-phase ligation-purification method is adopted, in which nucleic acid molecules are fixed on the surface of beads or other solid particles in order to rapidly purify products obtained from the ligation reaction.

Figure 1:
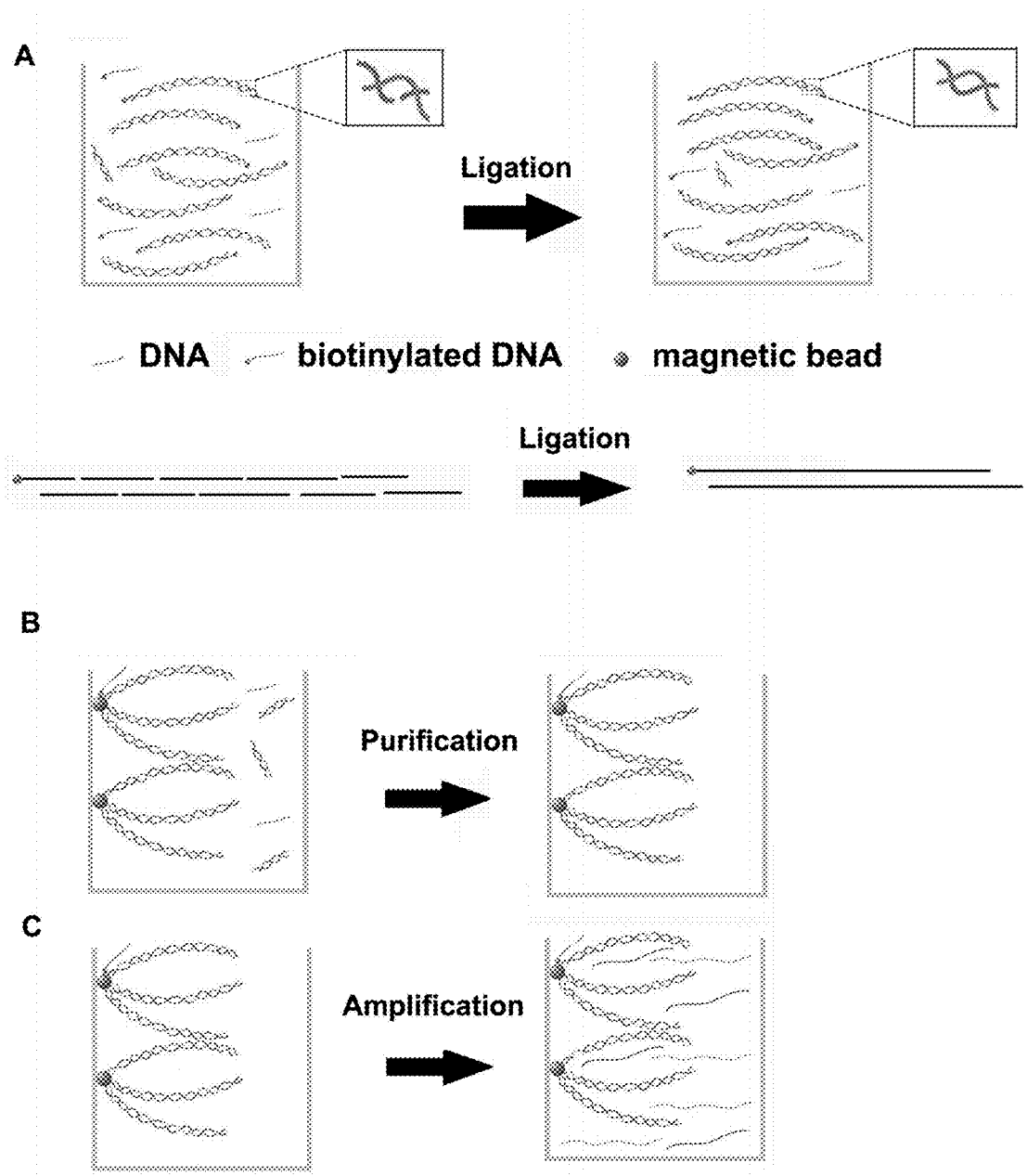
FIG. 1 is a schematic view of a method for synthesizing multiple oligonucleotides in accordance with an embodiment of the invention.

FIG. 1 shows a schematic view of a method of synthesizing multiple oligonucleotides in accordance with an embodiment of the invention. The technology comprises three steps: ligation, purification and amplification, as shown in A, B, and C, respectively. In Step A ("Ligation"), a set of oligomers are mixed and treated with phosphorylation, then ligated, with the ends of two neighboring DNA fragments being joined together by the formation of phosphodiester bonds between the 3'-hyroxyl of one DNA termini with the 5'-phosphoryl of another. In this example, to facilitate the purification of the ligated products, one of oligonucleotides was modified with biotin at the 5' end. These short-chain oligomers are subjected to annealing, and then ligation in the presence of a ligase, and finally form double-stranded nucleotide sequences. In Step B, magnetic beads modified with streptavidin are added to remove the substrates, incompletely connected products or mismatched products. Finally, in Step C, the purified products are amplified by use of PCR or other known amplification methods.

The term "amplification methods" may refer to any method in which oligonucleotides are used as templates and amplified in a linear or non-linear manner, including but not limited to PCR, transcription, isothermal amplification, and the like. PCR, also known as in vitro DNA amplification technique, includes three steps, denaturation, annealing and extension.

In embodiments of the invention, the short-chain nucleic acid molecules are first designed and synthesized. The long-chain nucleotide sequences to be assembled are divided into a group of double-stranded short-chain nucleic acid molecules. The long-chain nucleotide sequences are divided at points in a double-strand nucleotide sequence shifted from each other by at least between three and nine nucleotides. The more nucleotides between the divisions, the smaller the probability of mismatch becomes, thus increasing the accuracy of synthesis. The space of the division points along one strand preferably have the same length, but is dependent on the length of a short-chain nucleic acid molecule that can be synthesized by use of the current art. Since the methods for synthesizing single strand short-chain nucleic acid molecules are well known in the art, the cost is very low. For example, as one million oligonucleotides with 60 bp in length cost only a few of hundreds US dollars. That is, each base is less than one cent.

Long-chain nucleotide sequences are at least 2 times the length of the short-chain oligonucleotides. A long-chain nucleotide sequence typically comprises at least 700-1000 nucleotides, and each short chain nucleic acid molecules typically between 100-150 nucleotides. Synthesizing oligomers with a length of no more than 200 nucleotides is known in the art, such as from Agilent, LC science, etc.

In embodiments of the invention, the short-chain oligonucleotide is modified with a chemical group, or "purification oligonucleotide." In addition, modified solid particles with an affinity for the modified purification oligonucleotide may also be present. In embodiments of the invention, for example, the purification oligonucleotide could be modified with biotin while the solid particles are modified with streptavidin. In an embodiment of the invention, the purification oligonucleotide may be modified with amino group and solid particles modified with a carboxyl group. In one example, the purification oligonucleotide could be modified with azide group and solid particles modified with an alkyne group (or vice versa).

The short-chain oligonucleotides with a chemical group will be immobilized by the modified solid particles. The solid particles may include, but are not limited to, magnetic materials, silicon, silicon dioxide, ceramics, polymers, silica or glass. In fact, any known solid material capable of having its surface chemically modified as described herein can be used. "Immobilization" refers to a process in which the nucleic acid molecule is closely linked to the solid mass through a covalent bond between a nucleic acid molecule with a first chemical group (e.g., amino-NH2) and a solid body with a second chemical group (such as a carboxyl-COOH). Alternatively, the nucleic acid molecule may be closely linked to the solid mass by forming a non-covalent bond with high affinity between a nucleic acid molecule and a solid body (e.g., such as a nucleic acid molecule modified with biotin molecules and a solid body modified with avidin or streptavidin).

The short-chain oligonucleotides are then assembled into long-chain nucleotide sequences. The single-strand short-chain oligonucleotide is mixed in solution to form double-stranded "sticky end" nucleic acid molecules, since blunt-end ligation is much less efficient than sticky end ligation. These sticky-end double-stranded nucleic acid molecules may be ligated in the action of ligase to form a complete double-stranded long-chain nucleotide sequence. In embodiments of the invention, the ligase might be T4 DNA ligase or Taq ligase.

To purify the assembled long-chain nucleotide sequences, the long-chain nucleic acid molecules immobilized on the solid particles are incubated with the solid particles, and then rinsed with the buffer. Besides the solid-particle based purification method mentioned above, the nucleic acid molecule can be purified by using conventional high performance liquid chromatography ("HPLC"), polyacrylamide gel electrophoresis ("PAGE"), capillary electrophoresis or gel electrophoresis method, or any other method known in the art. In an embodiment of the invention, the purification step includes a transcription step in order to enhance the accuracy of amplified products or to reduce costs, since only expected ligation transcripts would be reverse-transcribed and amplified later. That is, the additional transcription and reverse-transcription performance can remove transcripts without a correct nucleotide sequence at the 3' terminal.

At the amplification step, the nucleic acid molecules immobilized on solid particles can be amplified by use of a known amplification method, such as PCR.

In embodiments of the invention, the 5' or 3' terminals of the assembled long-chain nucleic acid molecule can be removed by use of enzymes. If the amplified long-chain nucleotide sequences comprise the extra sequences used for purification and amplification other than the expected nucleotide sequence, these extra sequences could be removed through enzymatic digestion. If the amplified long-chain nucleotide sequences are the expected nucleotide sequences, this step may not be necessary.

The advantage of the present invention over the traditional methods lies in the purification of assembled nucleic acid molecules prior to amplification. If there are any mismatched pairs between DNA bases, the assembled long-chain nucleic acid molecules may contain randomly assembled products, incompletely ligated products or mismatched products. Performing the amplification step after the assembly step, without purification, means that many more by-products are produced. This not only wastes raw materials, but also greatly increases the difficulty and cost of separation. However, current systems and methods for synthesizing long-chain oligonucleotides have traditionally been immediately amplified before purification, resulting in a small number of expected long-chain nucleic acid molecules at a high cost.

In the present invention, synthesized long-chain nucleic acid molecules purified prior to amplification results in a significant decrease in the unexpected nucleic acid molecules, including randomly assembled products, incompletely connected products or mismatched products. This increases the yield of the expected long-chain nucleic acid molecules.

Up until now, although the synthesis of short chain nucleic acid molecules (less than 200 nucleotides) is easy and low-cost, the cost to obtain longer nucleic acid molecules is dramatically higher. Researchers have developed different strategies to obtain a certain number of long genes (such as Jindong Tian's group, which achieved 74 individual genes through physical separation, totally about 30 kb), but ultimately, the throughput capability is still subjected to the complexity and cost constraints. Because the present invention requires purification prior to amplification, it is feasible to perform the ligation, purification and amplification of hundreds of nucleotide sequences in parallel. And more importantly, the present invention does not increase cost and operational complexity.

As shown in FIGS. 2-8, the expected ligation products can be obtained even by use of initial oligonucleotides in low concentration such as 0.01 fmol/μL, which is critically important for the DNA oligonucleotides obtained from DNA microarray. The amount of DNA oligonucleotides synthesized in microarray is about 1 fmol per spot. Traditionally, to make use of these oligonucleotides for ligation, the amplification of these DNA oligonucleotides prior to ligation has been necessary.

Figure 2:
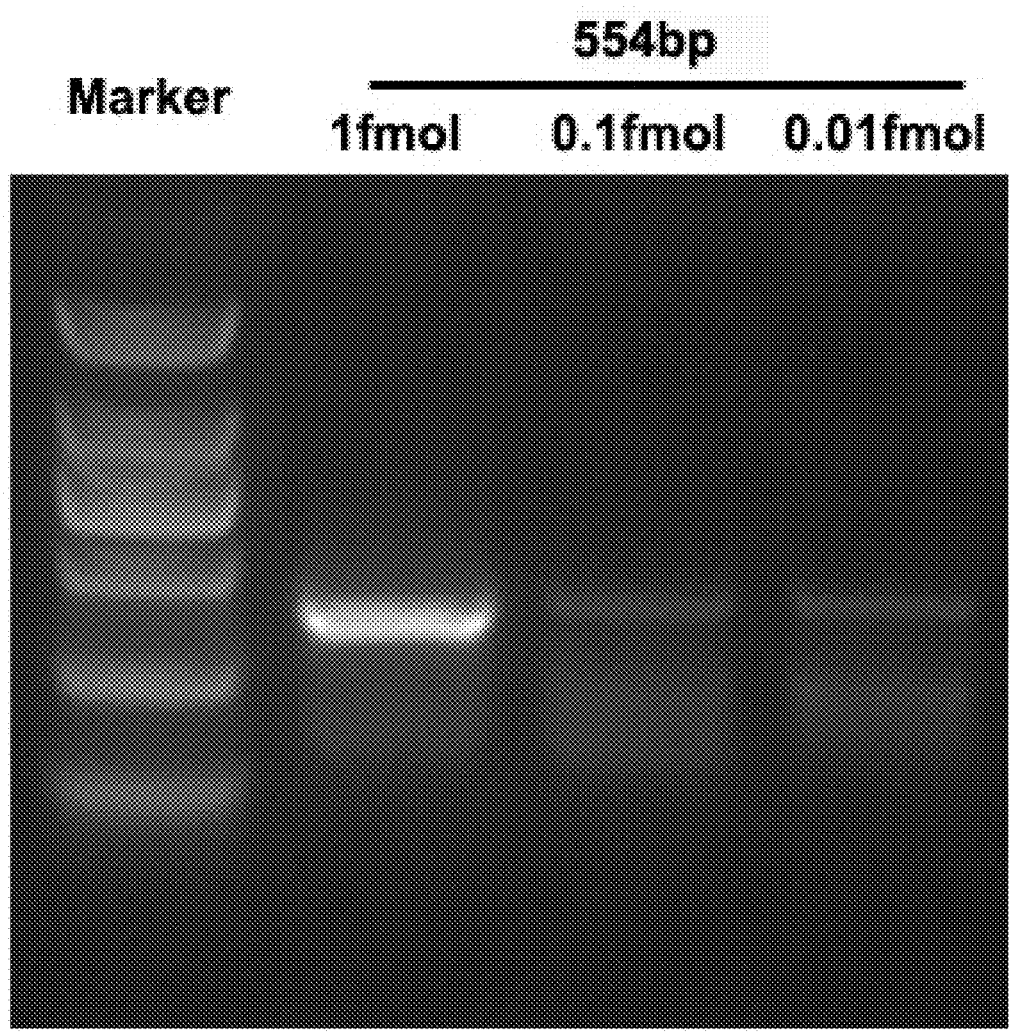
FIG. 2 shows the results of the synthesis of a single 554 bp DNA molecule in accordance with an embodiment of the invention.

For instance, FIG. 2 shows the results of the synthesis of a single 554 bp DNA molecule. A set of nucleic acid molecules with 25-59 nt in length (17), the linker sequences (1 and 2) and purification oligonucleotide (Table 1), were obtained and subjected to the LPA technique in accordance with embodiments of the invention. A single 554 bp DNA molecule was synthesized, which is confirmed by cloning and sequencing. Even if the initial amount of each nucleic acid molecule is as low as 0.01 fmol, the expected product can still be synthesized.

Figure 3:
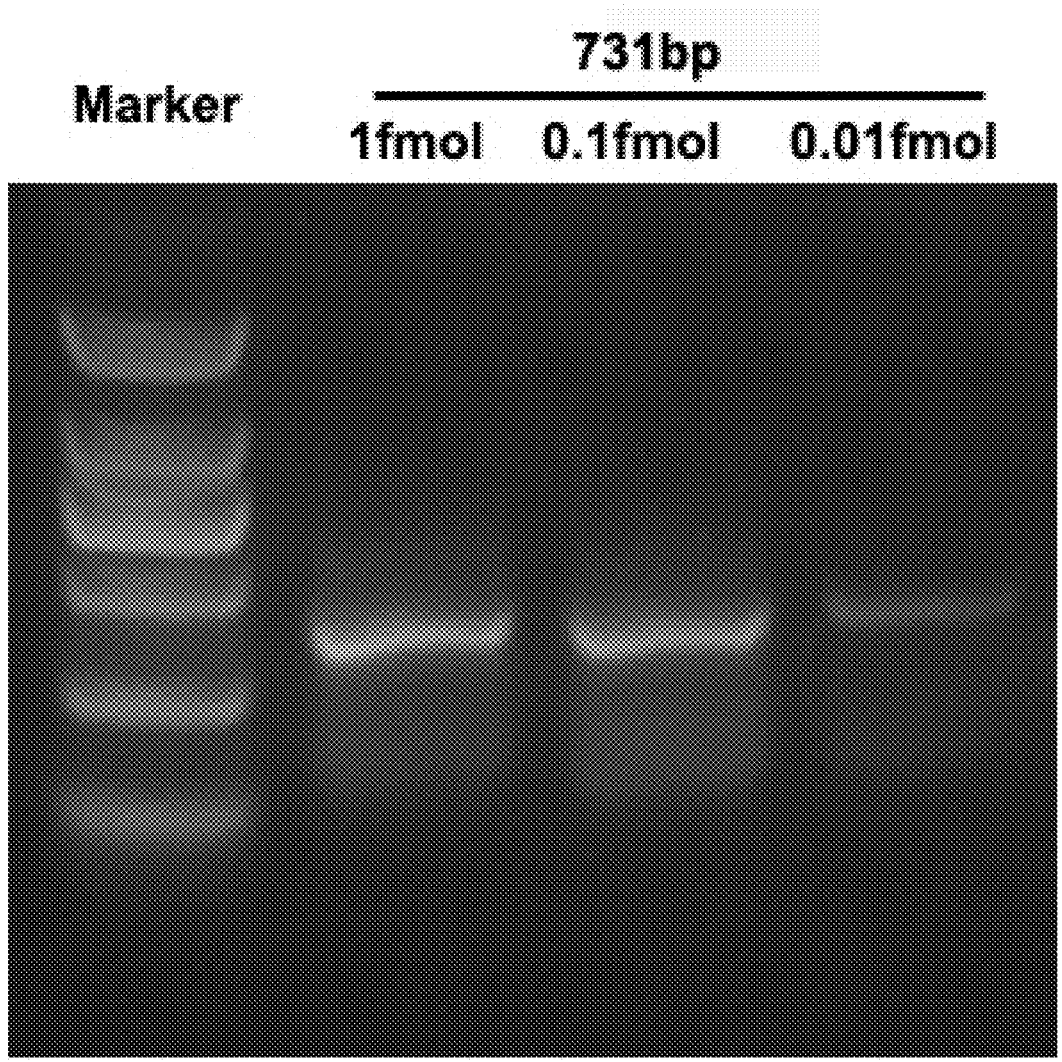
FIG. 3 shows the results of the synthesis of a single 731 bp DNA molecule in accordance with an embodiment of the invention.

FIG. 3 shows the results of the synthesis of a single 731 bp DNA molecule. A set of nucleic acid molecules with 25-60 nt in length (23), the linker sequences (1 and 2) and purification oligonucleotide (Table 2), were obtained and subjected to the LPA technique in accordance with embodiments of the invention. A single 731 bp DNA molecule was synthesized, which is confirmed by cloning and sequencing. Even if the initial amount of each nucleic acid molecule is as low as 0.01 fmol, the expected product can still be synthesized.

Figure 4:
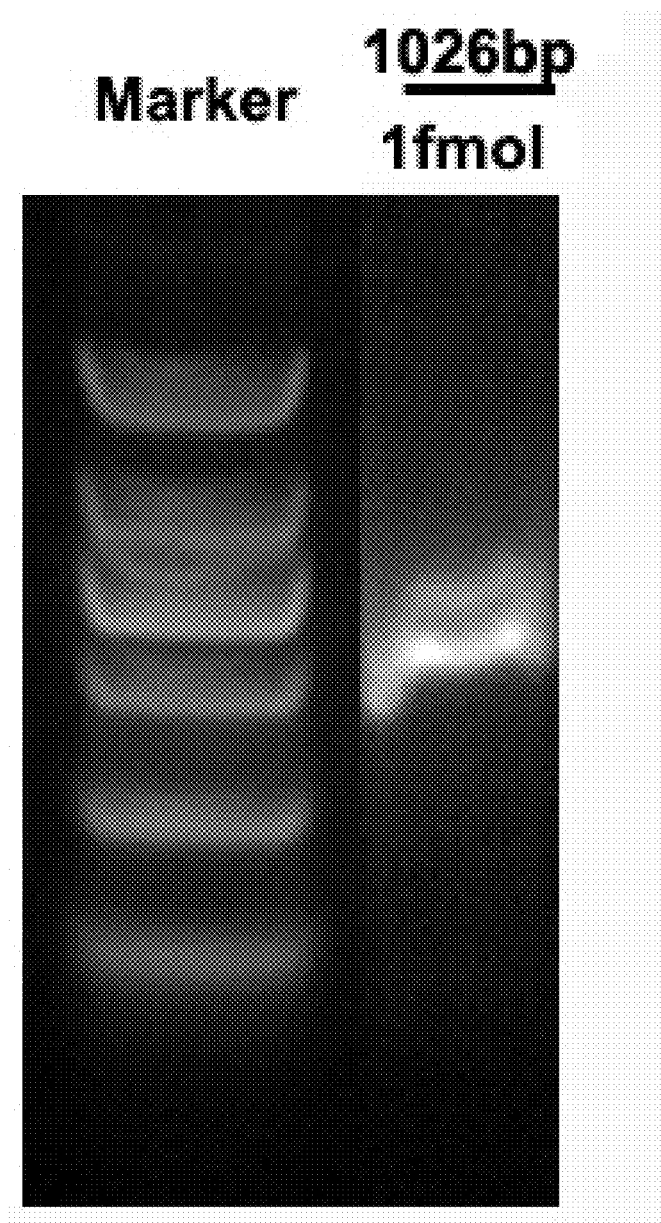
FIG. 4 shows the results of the synthesis of a single 1026 bp DNA molecule in accordance with an embodiment of the invention.

FIG. 4 shows the results of the synthesis of a single 1026 bp DNA molecule. A set of nucleic acid molecules with 25-60 nt in length (33), the linker sequences (1 and 2) and purification oligonucleotide (Table 3), were obtained and subjected to the LPA technique in accordance with embodiments of the invention. A single 1026 bp DNA molecule was synthesized, confirmed by cloning and sequencing.

Figure 5:
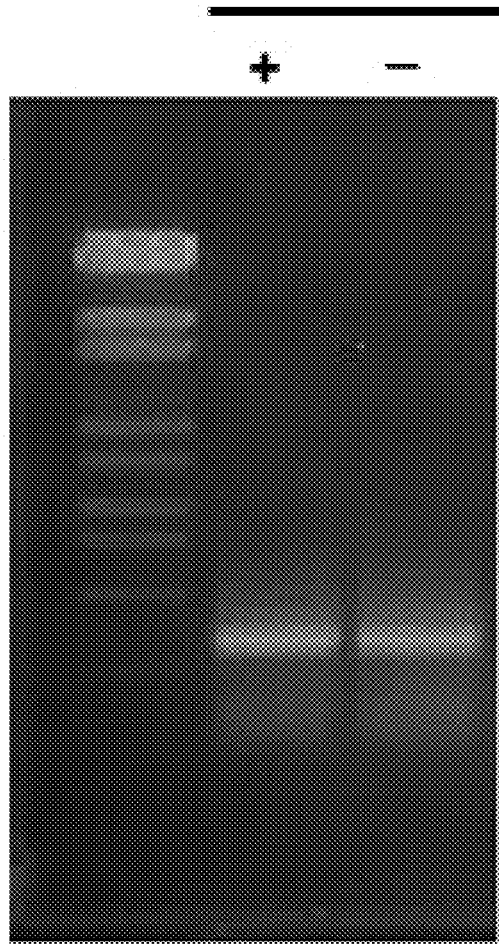
FIG. 5 shows the results of the synthesis of a single 554 bp DNA molecule in the absence of interference oligonucleotides, in accordance with an embodiment of the invention.

FIG. 5 shows the results of the synthesis of a single 554 bp DNA molecule in absence of interference oligonucleotides. A set of nucleic acid molecules with 25-59 nt in length (17), the linker sequences (1 and 2), purification oligonucleotide (Table 1) and a set of interference oligonucleotides (12) (Table 4), were obtained and subjected to the LPA technique in accordance with embodiments of the invention. A single 554 bp DNA molecule was synthesized, confirmed by cloning and sequencing.

Figure 6:
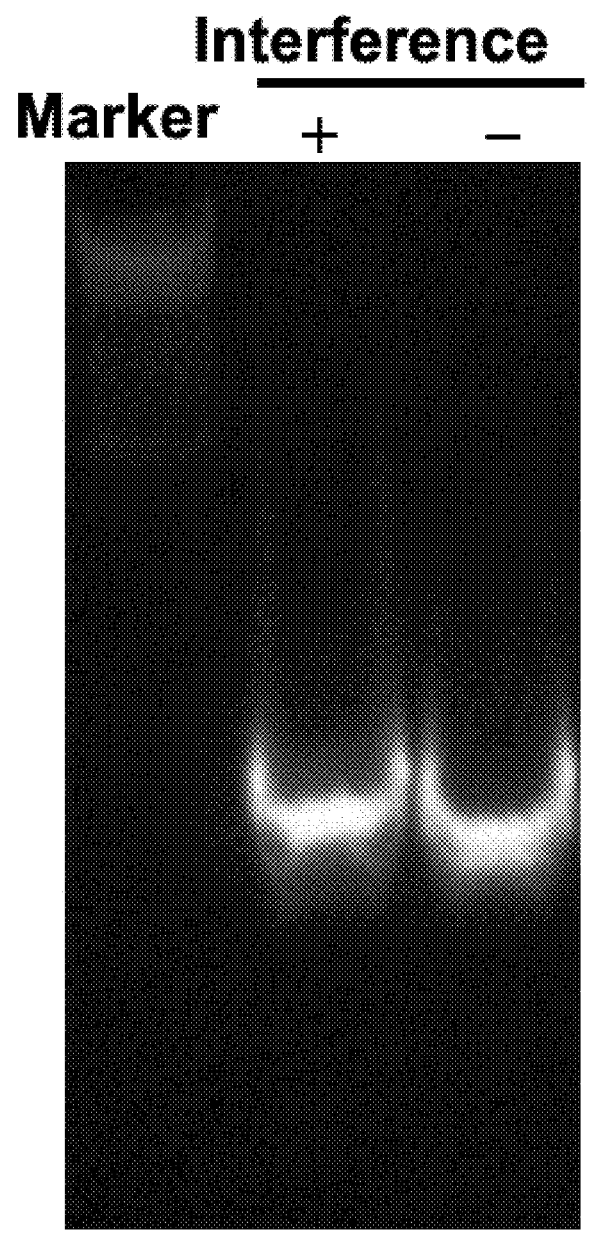
FIG. 6 shows the results of the synthesis of a single 731 bp DNA molecule in the absence of interference oligonucleotides, in accordance with an embodiment of the invention.

FIG. 6 shows the results of the synthesis of a single 731 bp DNA molecule in absence of interference oligonucleotides. A set of nucleic acid molecules with 25-59 nt in length (23), the linker sequences (1 and 2), purification oligonucleotide (Table 2) and a set of interference oligonucleotides (6) (Table 5), were obtained and subjected to the LPA technique in accordance with embodiments of the invention. A single 731 bp DNA molecule was synthesized, confirmed by cloning and sequencing.

Figure 7:
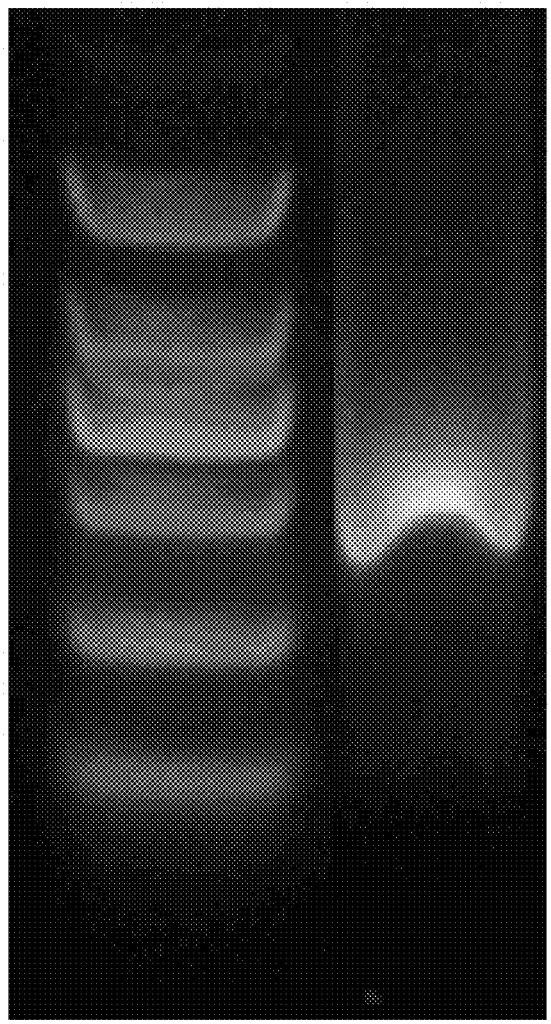
FIG. 7 shows the results of the synthesis of a single 1026 bp DNA molecule in the absence of interference oligonucleotides, in accordance with an embodiment of the invention.

FIG. 7 shows the results of the synthesis of a single 1026 bp DNA molecule in absence of interference oligonucleotides. A set of nucleic acid molecules with 25-60 nt in length (33), the linker sequences (1 and 2), purification oligonucleotide (Table 3) and a set of interference oligonucleotides (6) (Table 3), were obtained and subjected to the LPA technique in accordance with embodiments of the invention. A single 1026 bp DNA molecule was synthesized, confirmed by cloning and sequencing.

Figure 8:
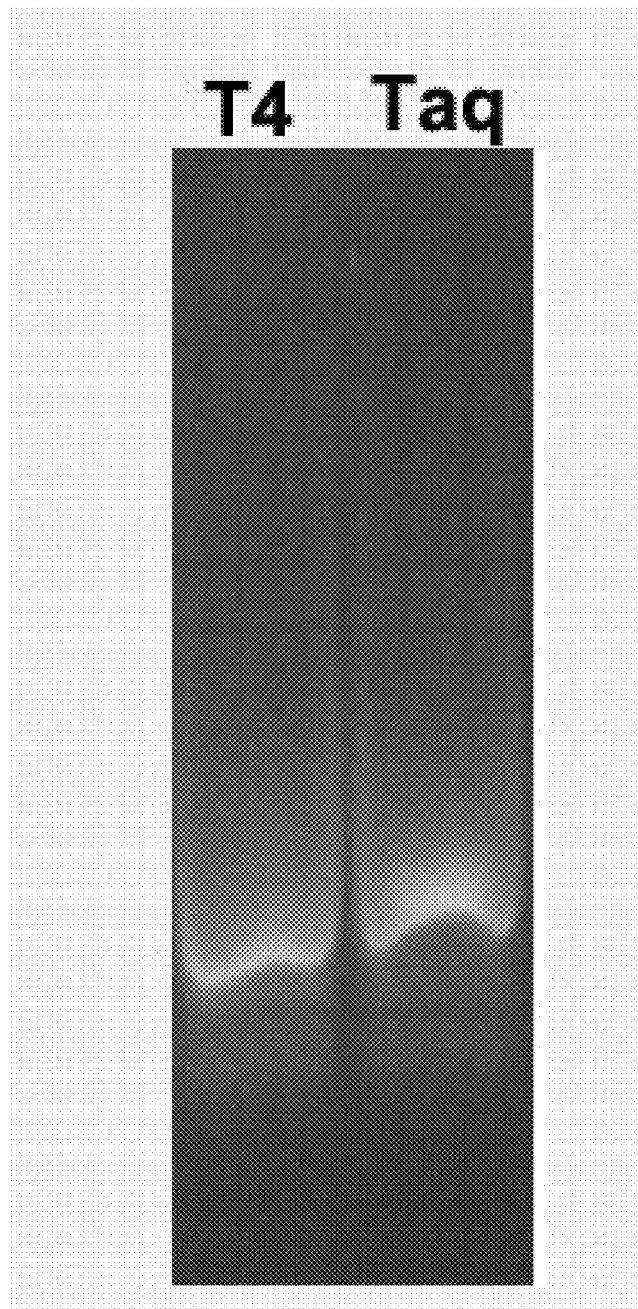
FIG. 8 shows the results of the synthesis of 554 bp, 731 bp, or 1026 bp DNA molecules in the absence of interference oligonucleotides, in accordance with an embodiment of the invention.

FIG. 8 shows the results of the synthesis of 554 bp, 731 bp, or 1026 bp DNA molecules in absence of interference oligonucleotides. A set of nucleic acid molecules with 25-60 nt in length (17+23+33=73), the linker sequences (1 and 2), purification oligonucleotide (1) and a set of interference oligonucleotides (12+6+6=24) (Tables 1-6), were obtained and subjected to the LPA technique in accordance with embodiments of the invention. Three DNA molecules, including 554 bp, 731 bp, or 1026 bp, were obtained, respectively, confirmed by cloning and sequencing.

The results in FIGS. 5-8 indicate that the method described in the present invention demonstrates particularly strong anti-interference capability. As shown Tables 4-6, a number of interference DNA oligonucleotides were added in these experiments. In each case, interference DNA oligonucleotides contained the same sequence as one of oligonucleotides to be assembled with the exception of 5 random nucleotides (N represents any of adenine, thymine, guanine or cytosine), which could generate significant interference to the complementary pairing between short-chain DNA oligonucleotides. Even so, the expected genes were successfully synthesized. Thus these results indicate that the systems and methods described herein have very strong anti-interference capability and are suitable for large-scale, high accuracy synthesis of long-chain nucleic acid molecules.

It will be readily understood by those persons skilled in the art that the present invention is susceptible to broad utility and application. Many embodiments and adaptations of the present invention other than those herein described, as well as many variations, modifications and equivalent arrangements, will be apparent from or reasonably suggested by the present invention and foregoing description thereof, without departing from the substance or scope of the invention.

Accordingly, while the present invention has been described here in detail in relation to its exemplary embodiments, it is to be understood that this disclosure is only illustrative and exemplary of the present invention and is made to provide an enabling disclosure of the invention. Accordingly, the foregoing disclosure is not intended to be construed or to limit the present invention or otherwise to exclude any other such embodiments, adaptations, variations, modifications and equivalent arrangements.

Examples of embodiments of the invention are described below.

Example A

A set of DNA oligonucleotides are dissolved in water solution, mixed and diluted to the concentration of 100 fmol/µl. These oligonucleotides are subjected to phosphorylation by using T4 kinase (Polynucleotide kinase, New England Biolabs (NEB), LTD), then incubated at 37° C. for 1 hour. After phosphorylation, all DNA oligonucleotides are further diluted to a concentration of each 1 fmol. Meanwhile, T1 beads (e.g., Dynal) are mixed with a purification oligonucleotide modified with biotin in 5' end, and incubated at room temperature for 15 minutes, then washed three times with buffer.

The phosphorylated DNA oligonucleotides are incubated with T1 beads immobilized with purification oligonucleotide at 65° C. for 2 hours. In order to ensure adequate hybridization between DNA oligonucleotides, the reactor is placed on top of a 220 rev/min shaker. The solution is slowly cooled to room temperature, and the beads washed to remove excess DNA oligonucleotides. Finally, T4 or Taq ligase was added into the solution, and the ligation reaction occurs overnight.

The ligated DNA products are then subjected to amplification through PCR, then the amplified products are purified, cloned and sequenced.

Example B

A set of nucleic acid molecules with 25-59 nt in length (17), the linker sequences (1 and 2) and purification oligonucleotide (Table 1), were first mixed and then subjected to phosphorylation. After annealing, a complete double stranded nucleic acid molecule can be formed in the presence of T4 ligase. Subsequently, the magnetic beads modified with streptavidin are used to purify the ligated products, which can effectively remove the reaction substrate, incompletely connected products or mismatched products. Finally, the purified products are enriched by use of nucleic acid amplification methods, such as PCR.

Example C

The magnetic beads are incubated with the purified oligonucleotide for 15 min, then washed three times with buffer. Then the beads mixed with other DNA oligonucleotides, and are treated following the same experimental procedure, such as ligation, purification and amplification described in Example B.

Example D

Following the same experimental procedure described in Example B, only the magnetic beads are changed to glass particles, polymer particles, such as poly (meth) acrylamide, poly lactic acid (PLA), polylactic acid-glycolic acid polymer ("PLGA"), polyacrylic acid ("PAA"), polymethacrylic acid, with 2-hydroxyethyl(meth)acrylate, poly-N-isopropyl (meth) acrylamide, vinyl acetate or polypropylene, or polyethylene amine.

Example E

A set of nucleic acid molecules with 25-59 nt in length (17), the linker sequences (1 and 2) and purification oligonucleotide (Table 1), are first mixed and then subjected to phosphorylation. After annealing, a complete double-stranded nucleic acid molecule can be formed in the action of T4 ligase. Subsequently, the product was purified by HPLC, which can effectively remove the reaction substrate, incompletely connected products or mismatched products. Finally, the purified products could be enriched by use of nucleic acid amplification methods, such as PCR.

Example F

Following the same experimental procedure described in Example B, only the HPLC purification was changed to use PAGE gel, gel electrophoresis, capillary electrophoresis or other purification methods.

Example G

Following the same experimental procedure described in Example B, except that a set of nucleic acid molecules with 25-59 nt in length (17), the linker sequences (1 and 2) and purification oligonucleotide (Table 1), 12 interference oligonucleotides (Table 5) are added. The purified products were subjected to cloning and sequencing.

Example H

Following the same experimental procedure described in Example G, only the initial nucleic acid molecules includes a set of nucleic acid molecules with 25-59 nt in length (totally 73), the linker sequences (1 and 2), purification oligonucleotide (1) and a set of interference sequences (totally 24) (Tables 1-6). The purified products were subjected to cloning and sequencing.

In the examples for which the sequence listings are attached herein, the following PCR primers were used: TCGAGCGGCCGCCCGGGCAGGT (as forward primer) (SEQ ID NO: 1); AGCGTGGTCGCGGCCGAGGT (as reverse primer) (SEQ ID NO: 2).

The invention claimed is:

1. A method for synthesizing long-chain nucleic acid molecules through assembling short-chain oligonucleotides, the method comprising:
   phosphorylating a set of short-chain oligonucleotides;
   modifying at least one of the short-chain oligonucleotides in the set with a first chemical group;
   annealing the set of short-chain oligonucleotides;
   ligating the set of short-chain oligonucleotides in the presence of a ligase, wherein the ligation produces at least one double-stranded long-chain nucleotide sequence;
   immobilizing the at least one double-stranded long-chain nucleotide sequence on solid particles modified with a second chemical group, wherein the first chemical group and second chemical group have an affinity for one another;
   purifying the at least one double-stranded long-chain nucleotide sequence, said purifying step including a transcription step followed by a subsequent reverse-transcription step;
   after purification, amplifying the at least one double-stranded long-chain nucleotide sequence.

2. The method of claim 1, further comprising the step of removing the terminal end of the at least one double-stranded long-chain nucleotide sequence through use of an enzyme.

3. The method of claim 1, wherein the at least one double-stranded long-chain nucleotide sequence is the entire nucleotide sequence to be synthesized.

4. The method of claim 1, wherein the at least one double-stranded long-chain nucleotide sequence is comprised of the nucleotide sequence to be synthesized as well as two flanking sequences comprising at least one PCR primer sequence and one oligonucleotide.

5. The method of claim 1, wherein the purification step is performed again after amplification.

6. The method of claim 1, wherein the solid particles comprise at least one of the following: silicon, silicon dioxide, ceramics, polymers, silica or glass.

7. The method of claim 1, wherein the first chemical group comprises with biotin and the second chemical group comprises streptavidin.

8. The method of claim 1, wherein the first chemical group comprises an amino group and the second chemical group comprises a carboxyl group.

9. The method of claim 1, wherein the first chemical group comprises an azide group and the second chemical group comprises an alkyne group.

10. The method of claim 1, wherein the ligase comprises at least one of the following: a T4 DNA ligase or Taq ligase, a derivative of T4 DNA ligase, or a derivative of Taq ligase.

11. The method of claim 1, further comprising purifying the assembled nucleic acid molecules by at least one of the following methods: HPLC, PAGE, capillary electrophoresis or gel electrophoresis.

* * * * *